(12) United States Patent
Mittal et al.

(10) Patent No.: US 10,292,679 B2
(45) Date of Patent: May 21, 2019

(54) DOPPLER ULTRASOUND BASED FETAL MONITORING

(75) Inventors: Chetan Mittal, Jalandhar (IN); Balasundar Iyyavu Raju, Chester, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 867 days.

(21) Appl. No.: 13/879,045

(22) PCT Filed: Oct. 17, 2011

(86) PCT No.: PCT/IB2011/054587
§ 371 (c)(1),
(2), (4) Date: Apr. 12, 2013

(87) PCT Pub. No.: WO2012/052904
PCT Pub. Date: Apr. 26, 2012

(65) Prior Publication Data
US 2013/0197362 A1    Aug. 1, 2013

(30) Foreign Application Priority Data
Oct. 19, 2010   (EP) .................................... 10188040

(51) Int. Cl.
*A61B 5/00* (2006.01)
*A61B 8/08* (2006.01)
*A61B 8/00* (2006.01)

(52) U.S. Cl.
CPC .............. *A61B 8/0866* (2013.01); *A61B 8/08* (2013.01); *A61B 8/4427* (2013.01); *A61B 8/46* (2013.01); *A61B 8/488* (2013.01); *A61B 8/54* (2013.01)

(58) Field of Classification Search
CPC ...... A61B 5/4362; A61B 8/0866; A61B 8/543
(Continued)

(56) References Cited

U.S. PATENT DOCUMENTS 4,603,702 A    8/1986   Hwang et al.
4,781,200 A *  11/1988  Baker .......................... 600/483
(Continued)

FOREIGN PATENT DOCUMENTS

CN    201085633    7/2008
EP    1852058      11/2007
(Continued)

OTHER PUBLICATIONS

G.T. Haar et al., "Ultrasonic Imaging: Safety Considerations", Interface Focus, vol. 1, No. 4, Aug. 6, 2011, pp. 686-697.
(Continued)

*Primary Examiner* — Rajeev P Siripurapu

(57) ABSTRACT

A fetal movement monitoring method that limits the ultrasound radiation to safe levels and conforms to the ALARA principle is disclosed. The disclosed method of monitoring fetal movements by Doppler ultrasound comprises accumulating the time for which ultrasound is radiated into a subject, comparing the accumulated time with a first reference total time, counting the number of fetal movements in the subject, comparing the number of movements with a reference number, deciding at least one of a further action of the device and an action to be recommended to the subject and conveying at least one of a further action of the device, an information to the subject about the counted fetal movements and an action recommended to the subject. A Doppler ultrasound device for monitoring fetal movements in a subject is also disclosed.

1 Claim, 4 Drawing Sheets

(58) Field of Classification Search
USPC .......................................................... 600/438
See application file for complete search history.

(56) References Cited

U.S. PATENT DOCUMENTS

| | | | |
|---|---|---|---|
| 6,045,500 | A * | 4/2000 | Bieniarz ........................ 600/300 |
| 7,338,446 | B2 * | 3/2008 | MacDonald et al. ......... 600/437 |
| 7,563,230 | B2 | 7/2009 | Nakaya et al. |
| 7,645,236 | B2 | 1/2010 | Simopoulos et al. |
| 8,641,626 | B2 | 2/2014 | Yoshida et al. |
| 2007/0102501 | A1 * | 5/2007 | Nguyen ........................ 235/1 R |
| 2008/0154155 | A1 | 6/2008 | Nishihara |
| 2010/0041994 | A1 | 2/2010 | Abe et al. |

FOREIGN PATENT DOCUMENTS

| | | |
|---|---|---|
| EP | 1680018 | 11/2008 |
| FR | 2602413 | 2/1988 |
| GB | 2225637 | 6/1990 |
| JP | 11089832 | 4/1999 |
| WO | WO199318710 | 9/1993 |

OTHER PUBLICATIONS

B. Karlsson et al., "The DopFet System: A new Ultrasonic Doppler System for Monitoring and Characterization of Fetal Movement", Ultrasound in Medicine and Biology, New York, NY, US, vol. 26, No. 7, Sep. 1, 2000, pp. 1117-1124.

E. Ryo et al., "A New Method for Long-Term Home Monitoring of Fetal movement by Pregnant Women Themselves", Medical Engineering & Physics, Oct. 1, 2011.

T. Wheeler et al., "Detection of Fetal movement Using Doppler Ultrasound", Obstetrics and Gynecology, Lippincott Williams & Wilkins, US, vol. 70, No. 2, Aug. 1, 1987, pp. 251-254.

* cited by examiner

| Col. 1 | Col. 2 | Col. 3 | Col. 4 | Col. 5 | Col. 6 | Col. 7 |
|---|---|---|---|---|---|---|
| Result of the first comparison (accumulated time < reference time > 0) | Result of the second comparison (COUNT* < reference count > 0) | Further action | Count normal or not | Recommendations to the subject | Example indication with a light source. For instance colored LED | Status of the device to be indicated to the subject |
| 0 | 0 | Continue counting movements | None | None | Blue/white | In use within first time slot |
| 0 | 1 | Stop US radiation and counting of movements | Normal | None | Green | Stopped |
| 1 | 0 (COUNT≥1) | Continue count | None | None | Amber | In extended time period |
| 1 | 0 (COUNT=0) | Stop counting movements | No fetal movement | Consult doctor | Red | Stopped |
| 1 | 1 | Stop counting | Normal | None | Green | Stopped |
| In the extended time period | | | | | | |
| (accumulated time < (reference time + extended time) > 0) | | | | | | |
| 0 | 1 | Stop counting movements | Normal | None | Green | Stopped |
| 1 | 0 | Stop counting movements | Fetal movement count below normal | Consult your doctor immediately | Red | Stopped |
| 1 | 0 | Stop counting | Normal | None | Green | Stopped |

*: COUNT = Counted number of movements

FIG. 2

DOPPLER ULTRASOUND BASED FETAL MONITORING

FIELD OF THE INVENTION

The following belongs to the field of Doppler ultrasound and to the field of Doppler ultrasound based fetal monitoring.

BACKGROUND OF THE INVENTION

With advances in ultrasound technologies, ultrasound monitoring devices are increasingly available for home use. With this, the risk of exposure to doses of ultrasound higher than recommended is also increasing. Home ultrasound devices with automatic time out and those that measure the dosage and automatically lock themselves are known. The principle behind safe exposure to any radiation, in the present case to ultrasound radiation, is known as ALARA—As Low As Reasonably Achievable.

The published European patent application EP1852058A1 titled "Fetus Movement Monitoring System and Fetus Movement Information Collecting Device" describes a device for sensing fetal movements that uses a passive sensor. It states that in hospitals, the image of a fetus in the uterus of the mother's body is generally monitored by an ultrasonic wave echo device. But, because this type of device is a so-called active sensor type which applies an ultrasonic wave to a fetus in the uterus of the mother's body and receives its reflected wave, it is undesirable to use this type of device for monitoring fetal movements over a long time in consideration of an adverse influence to the fetus. Furthermore, there is a problem that an ultrasonic wave echo device is configured to be used by a specialist such as a doctor or midwife, and cannot be used easily by a pregnant woman herself at home.

Recent advances in ultrasound technologies have enabled the use of Doppler Ultrasound for fetal movement monitoring at home. However the danger of unintended exposure to ultrasound radiation beyond recommended doses still exists.

SUMMARY OF THE INVENTION

It is preferable to have a Doppler ultrasound device and method and a computer program to execute such a method, for fetal monitoring at home that limits the ultrasound dosage to the recommended maximum daily dosage. It is also preferable to have such a device that also follows the ALARA principle.

Such a Doppler ultrasound device for monitoring a fetus in a subject and limiting ultrasound radiation to the fetus, comprises an estimator unit for estimating an adequacy of acoustic coupling between an ultrasound transducer and the subject, an accumulator unit for accumulating a time duration for which ultrasound is radiated into the subject, based on the estimate, a first comparison unit for comparing the accumulated time duration with a reference time duration, a detector unit for detecting a movement of the fetus based on reflected ultrasound radiation, a counter unit for counting the number of detected fetal movements, a second comparison unit for comparing the number of counted fetal movements with a reference number, a decision unit for making at least one decision based on at least one of an output of the first comparator and an output of the second comparator; and a user interface for conveying an information to the subject based on the at least one decision.

This device provides the advantage of being safe for use by the mother-to-be herself in the comfort of her home. It may further have the advantage of providing information about the movements of the fetus along with the information whether the movements are within the normal range or not. What is normal is based on available clinical data on the number of fetal movements in a given time duration. It may have the further advantage that the method follows the 'ALARA' principle and is safe for the mother-to-be and the fetus and, at the same time, provides information about fetal movements.

A method of Doppler ultrasound limiting ultrasound radiation to a fetus in a subject while monitoring the fetus, is also disclosed herein, the method comprising the steps of an estimation step of estimating acoustic coupling between an ultrasound transducer and the subject, an accumulation step of accumulating a time duration for which ultrasound is radiated into the subject, based on the estimation, a first comparison step of comparing the accumulated time duration with a first reference time duration, a detection step of detecting a movement of the fetus based on reflected ultrasound radiation, a counting step of counting the number of detected fetal movements, a second comparison step of comparing the number of counted fetal movements with a reference number, a decision step of making at least one decision based on at least one of the first comparison and the second comparison and a conveying step of conveying an information to the subject based on the decision.

A computer program product is also disclosed. The program comprises computer executable instructions for carrying out the disclosed method when the computer program is run on a computer.

A computer readable storage medium in which the disclosed computer program is stored is also disclosed.

BRIEF DESCRIPTION OF THE DRAWINGS

These and other aspects will be described in detail, by way of example, on the basis of the following embodiments and implementations, with reference to the accompanying drawings, wherein:

FIG. 2 is a table showing the functional details of the device disclosed;

DETAILED DESCRIPTION OF EMBODIMENTS

The disclosed device and method are described below in detail with reference to the figures.

Figure 1:
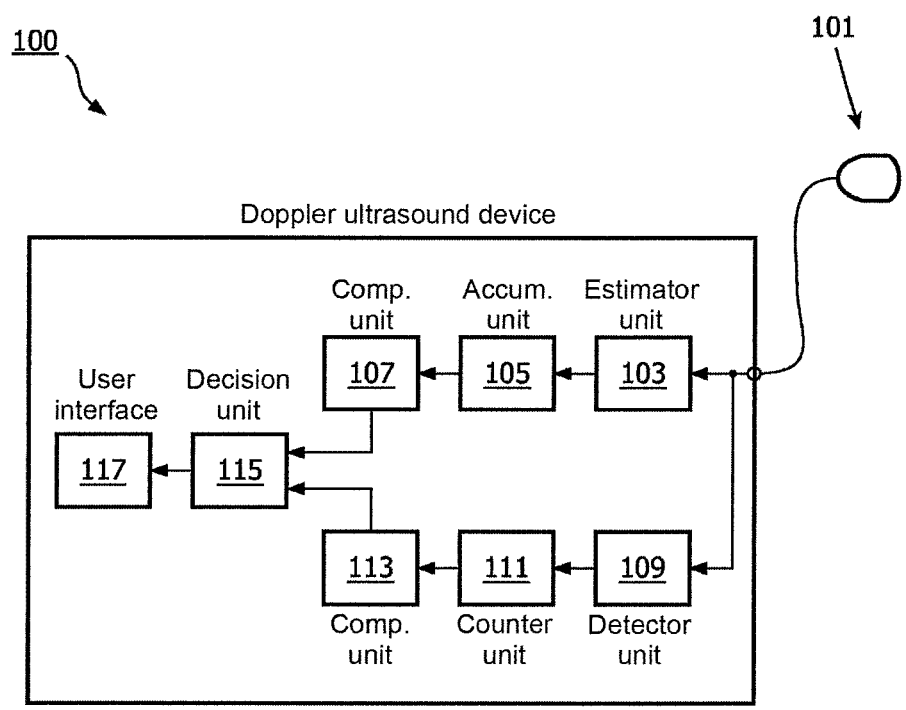
FIG. 1 is a diagrammatic representation of the device disclosed

With reference to FIG. 1, a Doppler ultrasound device 100 for assessing wellbeing of a fetus in a subject based on fetal movements is described. An ultrasound transducer 101 is used to radiate a subject with ultrasound of suitable characteristics and to receive the reflected ultrasound waves. The device comprises a estimator unit 103 for estimating whether the acoustic coupling between the transducer and the subject (not shown) is adequate or not. A accumulator unit 105 accumulates a time duration of ultrasound radiation. A first comparison unit 107 compares the accumulated time duration with a reference time duration. A detector unit 109 detects movements of the fetus based on reflected ultrasound radiation. A counter unit 111 counts the number of fetal movements detected by the detector unit 109. In one embodiment, the counter unit 111 counts fetal movements above a predefined threshold of at least one parameter of the movement of the fetus out of a set of parameters including but not limited to a magnitude, a velocity, an acceleration and a force. A second comparison unit 113 compares the number of counted fetal movements with a reference number. A decision unit 115 decides on at least one of a further action of the device, the assessed state of wellbeing of the fetus and an action recommended to the subject based on the comparison. A user interface 117 conveys the decision or decisions of the decision unit to the subject. The user interface 117 may also be used to convey to the user the estimate of the acoustic coupling from the estimation unit 103.

The various decisions and conditions under which those decisions are reached are now described. These conditions and decision are shown in tabular form in columns 1 to 5 of FIG. 2. If the number of counted movements reaches the reference number before the accumulated time duration for which ultrasound is radiated reaches the reference time duration, further counting of fetal movements is stopped. That is to say, ultrasound radiation is stopped and further ultrasound radiation is disabled for a predetermined time duration. This ensures that the exposure to ultrasound is limited according to the principle of ALARA. If the number of counted fetal movements does not reach the reference number before the accumulated time duration reaches the reference time duration, the following are done. The radiation of ultrasound and counting of the fetal movements is continued for a predefined extended time duration, say 30 minutes. The information that the fetal movement is being counted for the predefined extended time duration is conveyed to the subject. The counting is continued from the number that was reached when the reference time duration was reached. Whenever the number of counted fetal movements reaches the reference number at any time within the predefined extended time duration, it is conveyed to the subject that the number of fetal movements is within normal limits and further ultrasound radiation is disabled for the predetermined time duration. And if the number of counted fetal movements does not reach the reference number even at the end of the predefined extended time duration, the information is conveyed to the subject that the reference number has not been reached and the subject is recommended to consult a medical practitioner at the earliest and further ultrasound radiation is disabled for the predetermined time duration.

In an extreme case where not a single movement of the fetus is recorded when the accumulated time duration has reached the reference time duration, further radiation is disabled for the predetermined time duration and it is recommended to the subject to consult a medical practitioner at the earliest.

As described earlier, accumulator unit 105 starts accumulating the time duration of ultrasound radiation only when the estimator unit 103 has estimated that the acoustic coupling is adequate. Since the ultrasound transducer should be coupled adequately to the surface of the subject's abdomen, and an adequate amount of a gel between the surface of the abdomen and the transducer is needed to ensure adequate acoustic coupling, there are chances that the acoustic coupling is not adequate. Methods to determine whether the acoustic coupling is adequate or not, are known. They may utilize detection of ringing in the transducer when the acoustic coupling is inadequate, for instance.

Even though, in the description above, the time is said to be accumulated upwards, it is obvious that time can be counted downwards and when the remaining time reaches zero it is equivalent to the output of the first comparator indicating that the reference time duration has elapsed. The remaining time being greater than zero, conversely, is equivalent to the comparator indicating that the reference time duration has not elapsed. Thus the description is only to describe the method in an easily understandable manner. There may be many different ways of achieving the desired result and all such equivalent variations are assumed to fall under the scope of the disclosed method.

The conditions under which various actions are taken by the device, the indications to be conveyed to the subject and the recommendations to be made to the subject are listed in tabular form in FIG. 2. In this table, under the first two columns, the comparator output '1' means that the value of the corresponding compared quantity has reached or crossed the reference values of the respective comparators. Conversely the comparator output '0' indicates that the compared quantity is below the reference value. It is evident that this is only one way of describing the outputs and what is meant is a binary logical output.

The sixth column of the table in FIG. 2 shows the recommendations to be made to the subject under the various conditions described hitherto. The sixth column of FIG. 2 shows one of the exemplary ways of conveying information to the subject. Colored lights, LEDs for instance, are used to indicate various conditions and recommendations. However, other means of conveying information and recommendations to the subject could be thought of, for instance LED or LCD alphanumeric display units, for instance.

The disclosed device thus gives the subject information and recommends action to ensure the safety of the fetus and the subject. At the same time, it ensure that the subject cannot use the device further with the hope that if monitored further, the device may detect fetal movements and thereby wasting precious time in consulting a medical practitioner and/or endangering the subject and the fetus with radiation beyond the recommended maximum daily dosage.

In the description above, the reference number has been treated as a constant. However, it is known that as the pregnancy advances, the number of movements of the fetus per day, and hence the number of movements in the predetermined time duration tends to fall. Thus, the reference number reduces as the age of the pregnancy increases. The reference numbers may be updated as the age of the pregnancy increases. Reference numbers may be stored in a look up table, for instance, mapped to the age of the pregnancy and the reference number updated every time the device is used by the subject. Alternatively the reference number may be updated every week, once the age of the pregnancy has been entered at the time of the first use of the device.

Figure 3:
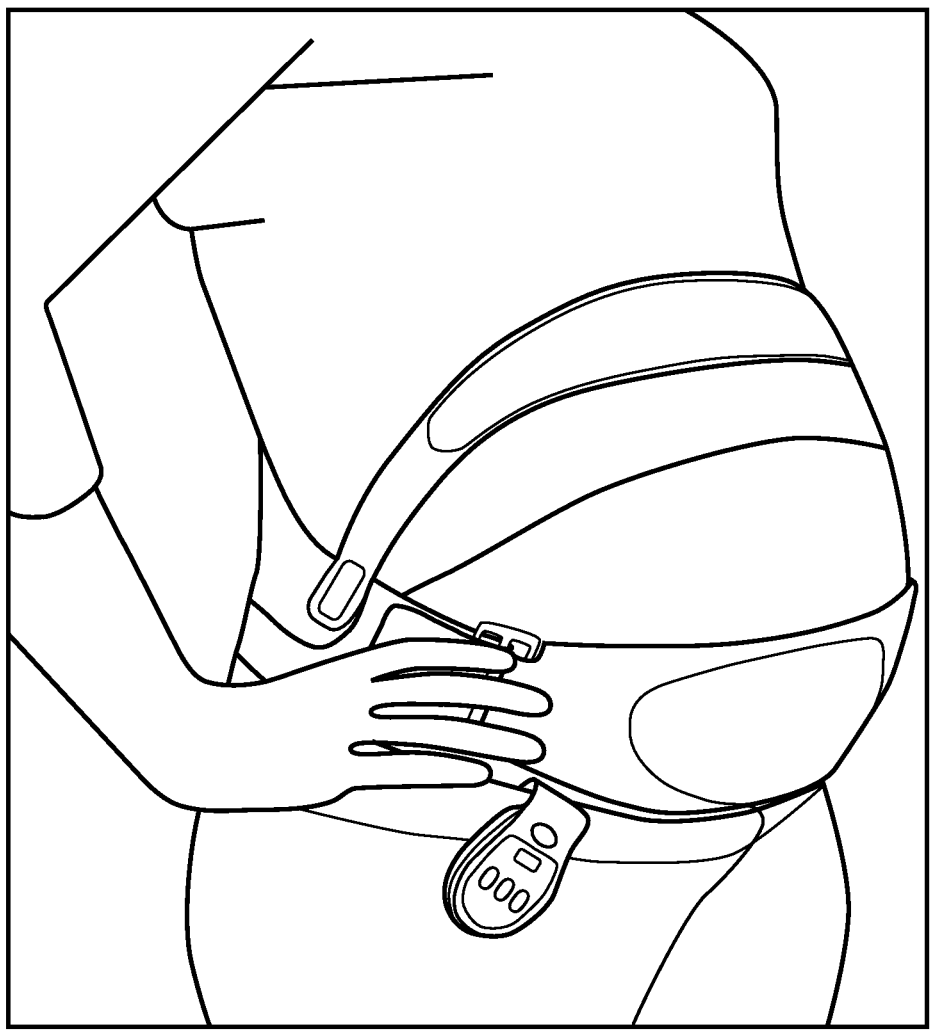
FIG. 3 is a diagrammatic representation of an embodiment of the disclosed device.

It is contemplated that the disclosed device is in the form of or comprises or adapted into a belt as shown in FIG. 3, which when worn around the waist or abdomen of the subject, positions the ultrasound transducer 315 on the surface of the subject's abdomen. However, the subject may have to ensure that gel is applied at the right place so that there is adequate acoustic coupling between the transducer and the subject. With this the subject can go about her work while the device is in operation.

Figure 4:
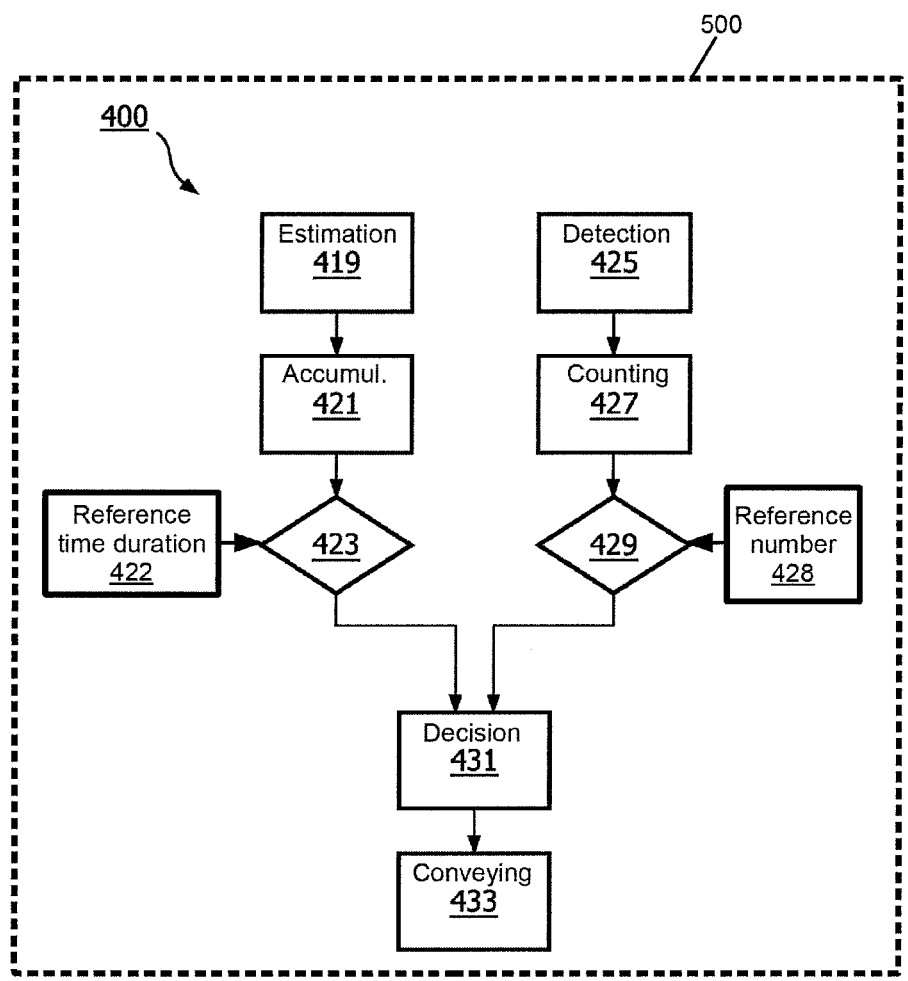
FIG. 4 is a diagrammatic representation of the method disclosed.

FIG. 4 is a diagrammatic representation of the disclosed method of Doppler ultrasound. It is known that ultrasound is radiated into a subject and the reflected waves are received and analyzed for imaging the part of the subject's body that reflects the ultrasound. If there are parts of the body that are moving inside the patient's body, the reflected ultrasound will have a shift in its frequency depending on the speed and direction of the movement of the part of the body. Such a shift is known as the Doppler shift. An analysis of the shift in the frequency, the Doppler shift, of the reflected ultrasound provides information on the movement of the parts of the subject's body.

According to the disclosed method 400, the abdomen of the subject is radiated with ultrasound and it is ascertained that the acoustic coupling between the ultrasound transducer and the abdomen of the subject is adequate in an estimation step 419. The duration of ultrasound radiation is measured and accumulated in an accumulation step 421 only when the estimate is that the acoustic coupling is adequate. This estimation is carried out periodically to ensure that the acoustic coupling remains adequate throughout the duration of the assessment. If the acoustic coupling is estimated to be inadequate at any time, the accumulation is stopped. It is continued only after the acoustic coupling has been set right. The accumulated time duration is compared with a reference time duration 422, one hour for instance, in a first comparison step 423. Simultaneously, the reflected ultrasound is received and analyzed to detect fetal movements in a detection step 425. The fetal movements sensed are counted in a counting step 427. The number of counted fetal movements is compared with a reference number 428 in a comparison step 429. Based on the results of the two comparisons, a decision is made in a decision making step 431. One of the decisions is whether to continue the process or not. The other decision is an estimate about the wellbeing of the fetus based on the number of counted fetal movements. One or more of these may be conveyed to the subject in a conveying step 433.

When this method is employed on a pregnant woman, with appropriate choice of the frequency of the ultrasound and the application of the ultrasound to the abdomen, information about the movements of the fetus may be obtained. This information may be about movements of the fetus, fetal heartbeat, maternal heartbeat blood flow in maternal or fetal blood vessels or both for instance.

Since the characteristics of the fetal movements are known, the signals corresponding to them can be recognized and counted. Although there are variations in the number of fetal movements from one mother-to-be to another, data on such movements collected over a large number of pregnant women has shown the normal evolution of the number of fetal movements over the gestation period. The trend of movements in a pregnancy is therefore relevant and any decrease of movements more than expected from the normal trend over the gestation period may be indicative of fetal compromise. Thus these movements may be counted to assess if the number of fetal movements in a given time duration is within the normal range or not.

However, if the number of fetal movements is below the normal count but is close to it, an ambiguity exists since the number of fetal movements is not uniform over the day. In such cases, the monitoring of the subject for fetal movements for an extended time is recommended. However, it is not recommended that the subject and the fetus be exposed to ultrasound over long periods of time. A method of Doppler ultrasound based fetal movement monitoring that avoids such exposure beyond the recommended dosage and still provides useful information about the fetal movement is disclosed.

A computer program product is also disclosed. Such a computer program product comprises computer executable instructions for carrying out the method 400 disclosed herein, when the computer program is run on a computer 500. The computer program has computer executable instructions to carry out the various steps of the disclosed method. The term computer is used in a general sense. This computer 500 could by any of the various digital circuits such as a microprocessor, microcontroller, a Digital Signal Processor (DSP) or any other dedicated or generally purpose electronic component with computing ability.

Computer readable media carrying the disclosed computer program is also disclosed. Such a computer program may be burnt or otherwise stored in computer readable media such as a CD, DVD, or a plug-in semiconductor memory device commonly called a USB device. The program may be made available on the internet for download and installed on the disclosed device before using the device. Such a program has all the necessary computer executable instructions to carry out the method either on a dedicated device such as the one disclosed above or on a general purpose Ultrasound device that could run the said program to carry out the various steps of the method disclosed.

While the embodiments and implementations have been described in detail in the drawings and description, such drawings and description are to be considered exemplary and not restrictive; the invention is not limited to the disclosed embodiments. Variations and combinations will occur to a practitioner and all such variations are deemed to be within the scope of the disclosed methods.

In the descriptions above, since the device and method are for use by a pregnant lady for monitoring herself, the term subject has been used everywhere. However it is conceivable that someone else may assist the lady and in that case, the information conveyed may be for that person. This however does not affect the descriptions in a significant manner.

Other variations to the disclosed embodiments can be understood and effected by those skilled in the art, in practicing the claimed invention, from a study of the drawings, the disclosure, and the appended claims. In the claims, the word "comprising" does not exclude elements or steps other than those mentioned, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope of the claims.

The invention claimed is:

1. A Doppler ultrasound device for monitoring a fetus in a subject and limiting ultrasound radiation to the fetus, the device comprising:
   an ultrasound transducer;
   a computer; and
   computer readable media storing instructions readable and executable by the computer to perform a fetus wellbeing assessment method, said instructions stored on the computer readable media including:
      instructions readable and executable by the computer to estimate an adequacy of acoustic coupling between the ultrasound transducer and the subject, accumulate a time duration for which ultrasound is radiated into the subject starting when the estimate indicates adequacy of the acoustic coupling, detect a movement of the fetus based on reflected ultrasound radiation, and count the number of detected fetal movements;

instructions readable and executable by the computer to stop the ultrasound radiation and disable further ultrasound radiation for a predetermined time duration upon the occurrence of the number of counted fetal movements equaling a reference number;

instructions readable and executable by the computer to stop the ultrasound radiation and disable further ultrasound radiation for a predetermined time duration upon the occurrence of the accumulated time duration equaling a reference time duration and the number of counted fetal movements equaling zero, and instructions readable and executable by the computer to stop the ultrasound radiation and disable further ultrasound radiation for a predetermined time duration upon the occurrence of the accumulated time duration equaling the sum of the reference time duration and a predefined extended time duration; and a user interface configured to convey information to the subject including at least a result of the fetus wellbeing assessment.

* * * * *